United States Patent [19]

Fukuzaki et al.

[11] Patent Number: 4,738,745
[45] Date of Patent: Apr. 19, 1988

[54] APPARATUS FOR MANUFACTURING MATERNITY PADS

[75] Inventors: Kenji Fukuzaki, Kawanoe; Takashi Ando, Kanonji, both of Japan

[73] Assignee: Daisho Iron Works Co., Ltd., Kawanoe, Japan

[21] Appl. No.: 33,108

[22] Filed: Mar. 31, 1987

[30] Foreign Application Priority Data

Jan. 19, 1987 [JP] Japan .................................. 61-11081

[51] Int. Cl.[4] ........................ B29C 43/04; B32B 31/20
[52] U.S. Cl. .................................... 156/500; 156/245; 156/510; 156/519; 156/522; 450/37; 450/39
[58] Field of Search ............... 156/196, 213, 224, 245, 156/500, 510, 517, 519, 522, 552, 553; 2/267; 264/257, 258, 320, 324; 450/1, 37, 39, 92, 93; 425/233, 236, 263, 264, 266, 346, 348 R, 351, 354, 412, 413, 422, 444; 604/358, 365, 366, 378, 379, 385.1, 385.2

[56] References Cited

U.S. PATENT DOCUMENTS

| | | | |
|---|---|---|---|
| 2,891,544 | 6/1959 | London | 450/37 |
| 2,896,623 | 7/1959 | Fitzgerald | 2/267 |
| 4,047,534 | 9/1977 | Tomaschefsky et al. | 450/37 |
| 4,074,721 | 2/1978 | Smits et al. | 450/37 |
| 4,193,404 | 3/1980 | Repke et al. | 604/366 |

*Primary Examiner*—Caleb Weston
*Attorney, Agent, or Firm*—Wenderoth, Lind & Ponack

[57] ABSTRACT

Maternity pads for absorbing excess mother milk spilled out are manufactured in a single assembly line, in which rolls of absorbent materials drawn out forward and stacked one upon another are die-cut into disks, which are then sent forward and placed onto a web of waterproof paper traveling ahead, while being covered by a web of covering material traveling in the same direction. The outside of the disks of absorbent materials are sealed and die-cut to obtain disks with the absorbent materials wrapped up in the waterproof paper and covering material. The disks are then transported to a shaping unit where they are formed into bowl-shaped pads by means of pairs of male and female molds. The finished maternity pads are removed from the line by a discharge means.

1 Claim, 5 Drawing Sheets

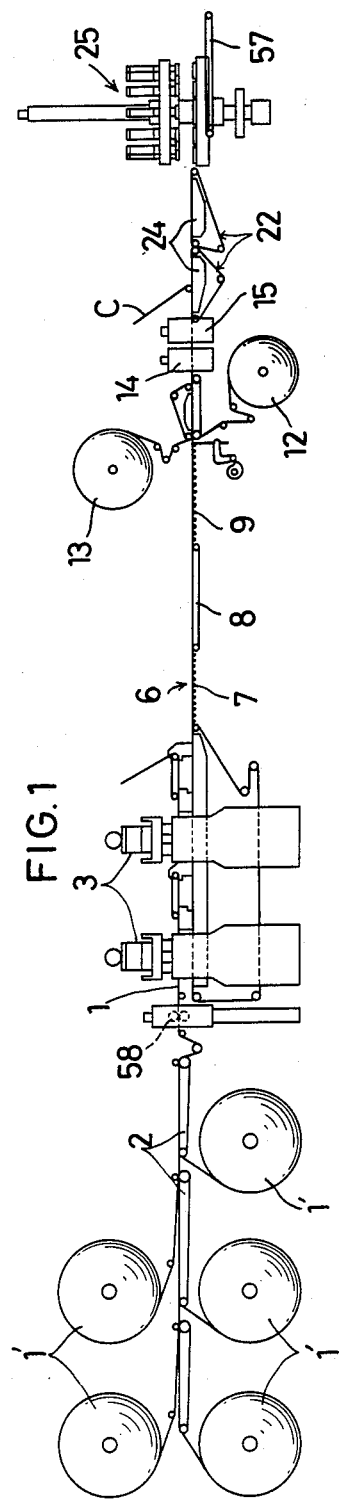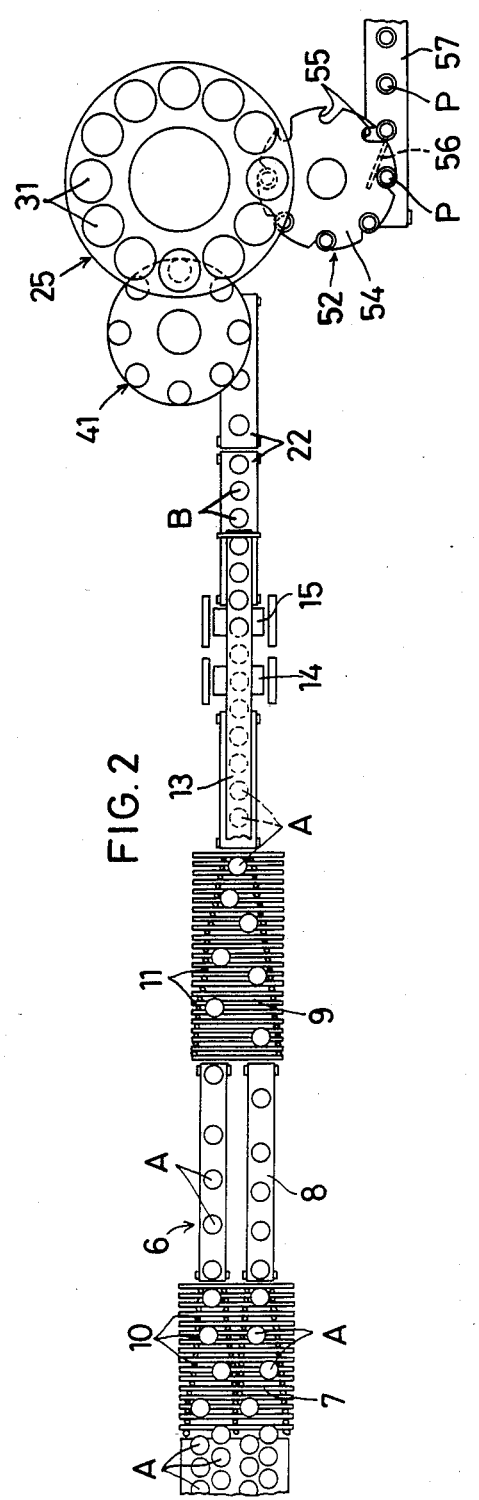

APPARATUS FOR MANUFACTURING MATERNITY PADS

The present invention relates to apparatus for manufacturing maternity pads for absorbing excess breast milk spilled out other than the time of feeding.

The Japanese Patent Publication No. 56-43426 discloses apparatus for manufacturing maternity pads of this type. On the conventional machine, a web of covering material of paper with polyethylene laminated thereon is fed on a belt conveyor driven intermittently. The first press forms nipple-fitting openings in the web when the web is at a stop. When the portion having the nipple-fitting opening comes to the second press, a male mold is lowered through a female mold to die-cut a plurality of webs of absorbent material supplied across the web of covering material, while a supporting rod raised above the female mold pushes up the webs of absorbent material to form them into a bowl shape. The absorbent material thus die-cut is lowered and heat-sealed to the web of covering material. This portion is then sent to a sealing unit where the second web of polyethylene paper fed over the absorbent material is heat-sealed to the web of covering material with the absorbent material wrapped up therebetween. The sealed portion is then die-cut by another press to obtain a pad.

Since the supporting rod is moved up through the nipple-fitting opening to push up only the central portion of the absorbent material, the latter is liable to be formed into a cone shape rather than such a bowl shape as to fit a breast. Another problem is that this apparatus requires two presses. The first press is for sealing the die-cut absorbent materials to the web of covering material. The second press is for sealing the second web of polyethylene paper to the first one. Furthermore, when the second web of polyethylene paper is sealed by the second press, the bowlshaped absorbent materials tend to be flattened under the influence of stretching force directed from the center of the second web of polyethylene paper toward its periphery which is produced while pressing.

In accordance with the present invention, the absorbent material is drawn out and sent to the first die cutter where it is cut into circular interior materials. They are fed on the first transportation aisle and placed on a waterproof paper. A covering material of unwoven cloth or the like is drawn out forward and laid on the waterproof paper. The interior materials are covered with the waterproof paper and the covering material.

While the covered interior materials are passing through a sealing device, it seals the waterproof paper to the covering material annularly outside of the periphery of each interior material so that the interior material will be completely covered. The assembly is then die-cut outside of the sealed portion by the second die cutter to obtain a disk. The disks are then feed on the second transportation aisle to its end where they are picked up by a feeder and placed on a rotating female mold. Then a male mold lowered by a shaping device presses the disk in cooperation with the female mold into a bowl-shaped pad with the covering material enclosed. The pads thus shaped are then raised up together with the ascending male mold and taken out by a discharge device.

Other features and objects of the present invention will become apparent from the following description with reference to the accompanying drawings, in which;

FIG. 1 is a side view showing the apparatus for manufacturing pads in accordance with the present invention;

FIG. 2 is a plan view of the same;

Figure 3:
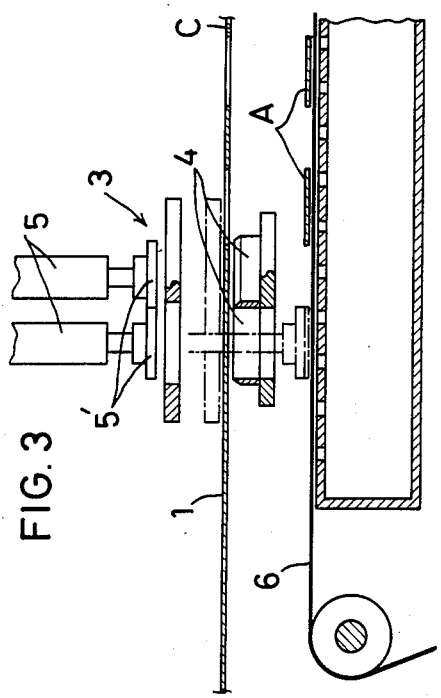
FIG. 3 is a vertical sectional side view of the first die cutter.

In the drawings, numeral 1 indicates an absorbent material of a predetermined thickness which is drawn out forward and fed. The absorbent material 1 comprises a predetermined number of water-absorbent papers which are adapted to be drawn out from rolls 1', piled up one upon another and fed on a belt conveyor 2.

Numeral 3 indicates the first die cutters for diecutting the absorbent materials into a disk shape. As shown in FIG. 3, the first die cutters 3 comprise cylindrical stationary knives 4 arranged beneath the absorbent material 1 and circular plates 5' arranged over the absorbent material 1 and adapted to go up and down by means of cylinders 5 so as to get into and out of the stationary knives 4. Though in this embodiment the absorbent material 1 is to be die-cut when they are at a halt, rotary die cutters may be used instead.

Figure 10:
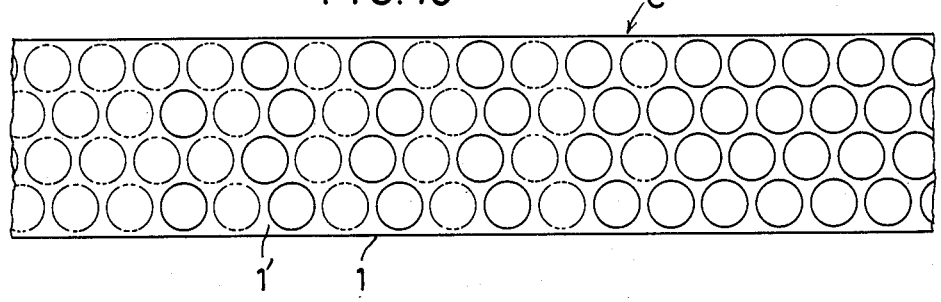
FIG. 10 is a plan view of the remainder left over after die-cutting.

Interior materials A die-cut by the first die cutters 3 are transported on the first transpotation aisle 6. There are two sets of the first die cutters 3 arranged in series to speed up the production. Furthermore, as shown in FIG. 10, a plurality of disc-shaped interior materials are adapted to be die-cut at one time. The first transportation aisle 6 comprises a low-speed conveyor 7, a medium-speed conveyor 8 and a high-speed conveyor 9 aligned in series in this order from the side of the die cutters. The interior materials A are divided into two rows on the low-speed conveyor 7 by means of rows of vertical rollers 10 arranged in two pairs of lines which are so adapted that as the conveyor proceeds, the width between each pair of the rollers becomes narrower. Then the materials A are transferred onto the medium-speed conveyor 8 where the spaces between two rows of the materials A are widened. They are then transferred onto the high-speed conveyor 9 where the two rows of the interior materials A are converging into a single row by means of rows of vertical rollers 11 so adapted that as the conveyor proceeds, the width between each pair of the rollers becomes narrower.

The interior materials A sent out of the first transportation aisle are transferred onto waterproof paper 12 drawn out of a roll while a covering material 13 of unwoven cloth drawn out of a roll are piled over the waterproof paper to cover the interior materials A.

On the way of the waterproof paper 12 and the covering material 13 are provided a sealing unit 14 for sealing the waterproof paper 12 to the covering material 13 with the interior materials wrapped up therein, and the second die-cutter 15 which die-cuts annularly the outer edges of the sealed portions of the waterproof paper 12 and the covering material 13 to give a disk B.

Figure 4:
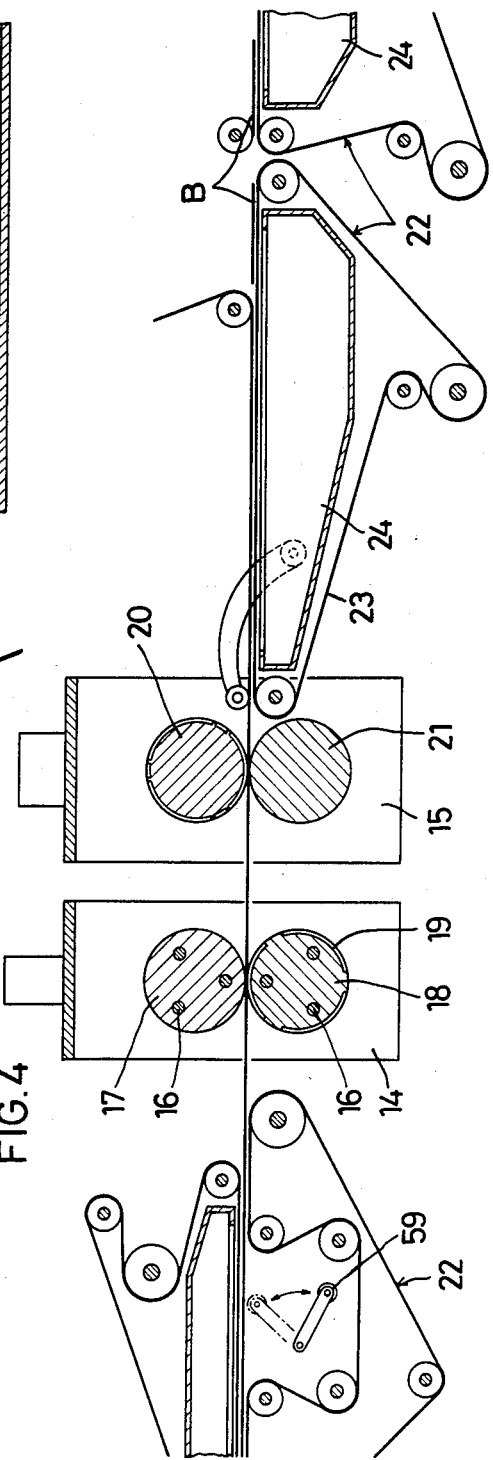
FIG. 4 is a vertical sectional side view of the sealing device and the second die cutter.

As shown in FIG. 4, the sealing unit 14 comprises a pair of heating rollers 17 and 18 including built-in heaters 16 and serving to drive the material. The lower heating roller 18 is formed with recesses 19 having a diameter slightly larger than the diameter of the interior materials A. The unit 14 seals the waterproof paper 12 to the covering material 13 at the outside of the edge of each interior material A.

The second die cutter 15 is a rotary die cutter comprising a cutter roll 20 provided with a drive unit and a receiving roll 21 shown in FIG. 4.

The discs B die-cut by the second die cutter 15 are then transported on the second transportation aisle 22 which comprises a net conveyor 23 and a suction box 24 serving to prevent the discs B on the net conveyor 23 from moving relative to one another.

The web remainder after the discs B have been die-cut is effectively rolled up. Ahead of the second transportation aisle 22 is provided a shaping machine 25 to form each disk B in a bowl shape with its waterproof paper side protruding so that the disk will fit a breast.

Figure 5:
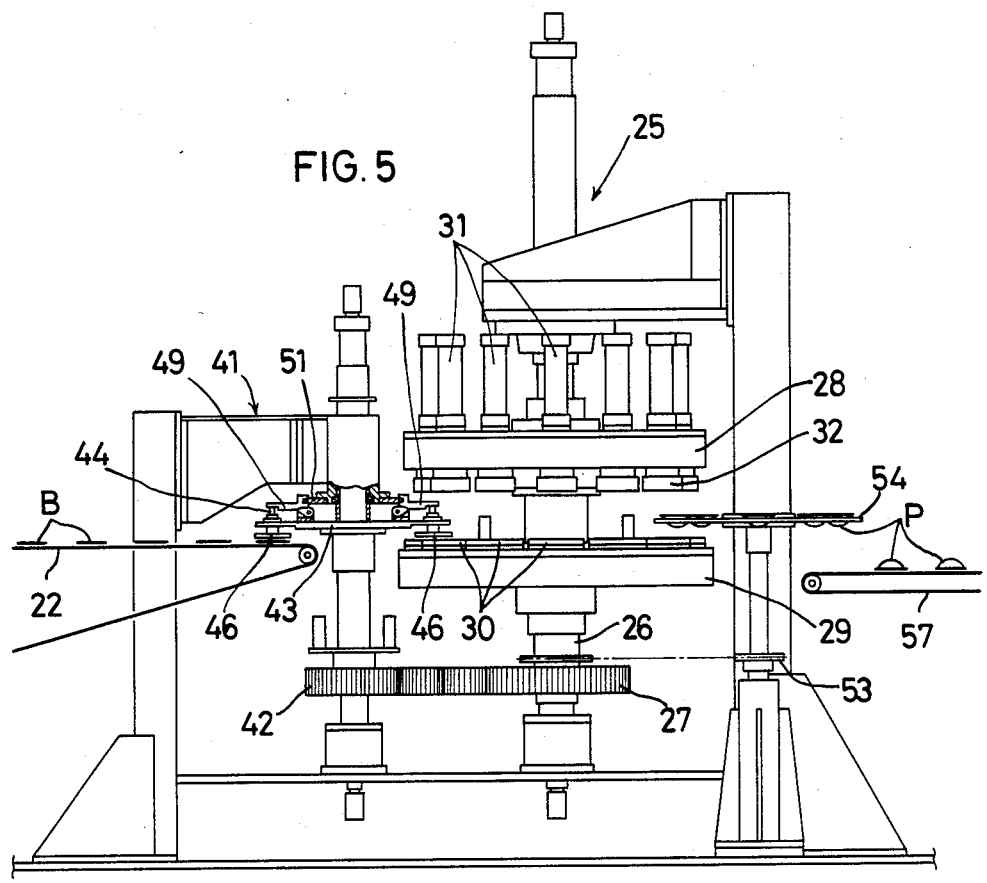
FIG. 5 is a partially cutaway side view showing a portion of the shaping machine.
Figure 6:
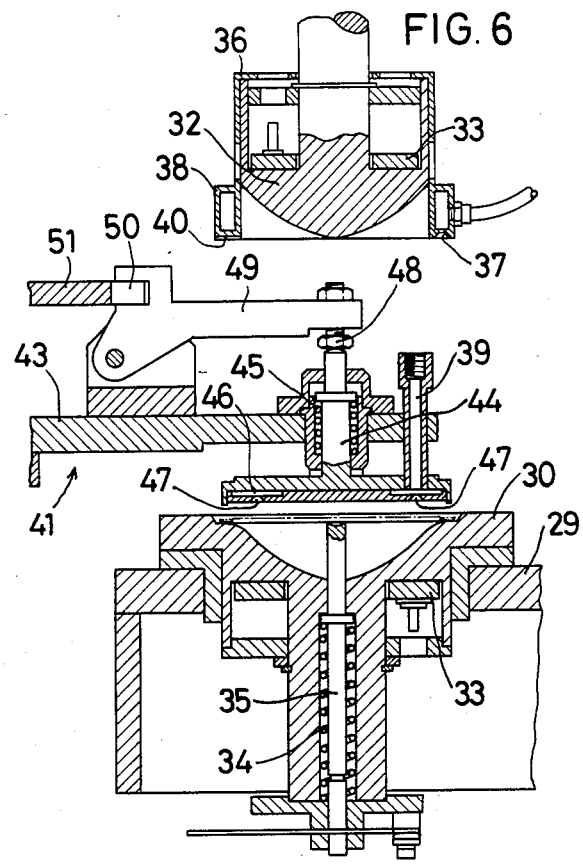
FIGS. 6 and 7 are enlarged vertical sectional side views showing portions the same.
Figure 7:
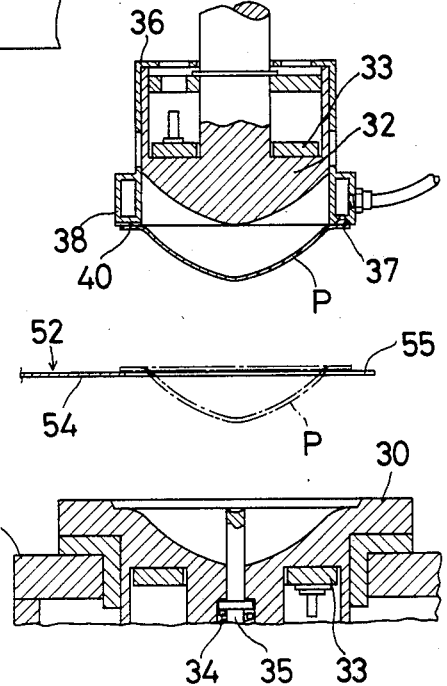
Figure 8:
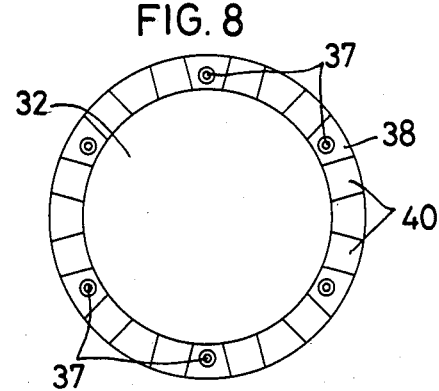
FIG. 8 is a bottom view of the male mold.
Figure 9:
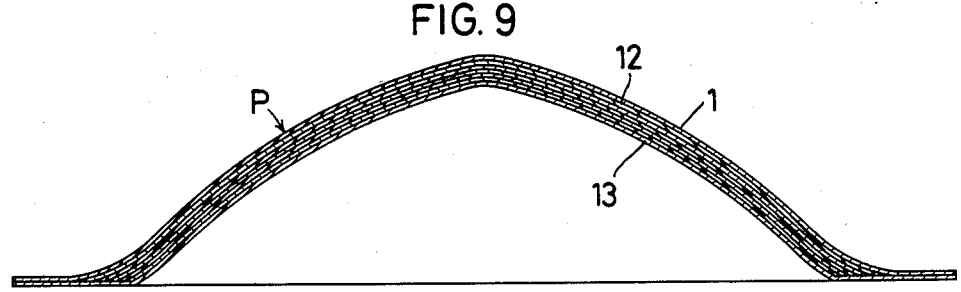
FIG. 9 is an enlarged vertical sectional front view of a pad.

As shown in FIGS. 5 to 7, the shaping machine 25 comprises a rotary shaft 26 rotated in one direction by means of a drive mechanism 27, an upper disk 28 and a lower disk 29 mounted on the rotary shaft 26, female molds 30 arranged on the peripheral portion of the lower disk 29 at equal angular intervals, male molds 32 arranged so as to be located right above the respective female molds and mounted on the periphery of the upper disk 28 at equal angular intervals so as to be movable up and down by actuators 31 such as cylinders, and heaters 33 mounted in the female molds 30 and the male molds 32. The disks B are sent onto the female molds 30, and then the male molds 32 are lowered by the actuators 31 to press the disks B between the female molds 30 and the male molds 32 into a bowl shape with their waterproof paper side protruding so they will just fit breasts.

The male molds 32 are then raised again after a predetermined period of time by means of the actuators 31.

An ejector pin 35 urged upwardly by a spring 34 may be provided in the center of each female mold 30 as shown in FIG. 6 in order to prevent the misalignment of each disk B while being pressed and to provide easy release of the pad P from each female mold 30. Further, a cylindrical member 36 may be provided around each male mold 32 and adapted to axially move relative to the male mold 32. An annular box 38 formed with an opening 37 in the bottom wall is provided under the member 36. Sucking the air from the box 38 through a hose connected to a port 39 will stick the pad P to the ascending male mold 32 and allow easy release of the pad from the female mold 30.

A passage 40 provided under the box 38 through which the inside of the cylindrical member 36 connects to the atmosphere will prevent an excessive pressure differential from building up between the inside and outside of the cylindrical member 36 (when the male mold 32 is raised with a pad stuck to the lower end of the cylindrical member 36), thus preventing the center of the pad P from being deformed by upward suction force.

Numeral 41 indicates a feeder to send the disks B which has reached the delivery end of the second transportation aisle 22, onto the female molds 30.

The feeder 41 comprises a disk 43 driven by a drive mechanism 42 in one direction, supporting shafts 44 mounted through the outer peripheral portion of the disk 43 at equal angular intervals so as to be vertically movable, springs 45 biassing the supporting shafts 44 upwardly, suction boxes 46 mounted on the lower end of the supporting shafts 44, suction ports 47 formed in the bottom walls of the boxes 46, rocking plates 49 having one end thereof pivoted on the disk 43 so that the lower end of the protruding shaft 48 formed at the other end will butt the upper end of the respective supporting shafts 44, and stop cams 51 contacting the rolling elements 50 at the inner ends of the rocking plates 49.

Upon the arrival of a disk B at the rear end of the second transportation aisle 22, one end of the rocking plate 49 for the box 46 located right over the disk B is lowered by the action of the protruding edge of the cam 51 and the rolling element 50. The protruding shaft 48 pushes down the box 46 until the bottom surface of the box 46 comes in contact with the upper surface of the disk B. Suction in the box 46 is started at the same time, sucking the disk B on to the lower surface of the box 46. The rolling element 50 is unhooked from the cam 51 simultaneouly, freeing the supporting shaft 44, so that the box 46 rises together with the supporting shaft 44 by the bias of the spring 45.

When the constantly rotating suction box 46 with the disk B stuck to it comes to the point right above the female mold 30, and the center of the female mold 30 comes in alignment with the center of the disk B, the rolling element 50 abuts the projecting edge of the cam 51, pushing down the supporting shaft 44 through the protruding shaft 48 and unload the disk B on to the female mold 30. Then the suction in the box 46 is released so as to leave the disk B on the female mold.

The box 46 with the disk B released rises with the supporting shaft 44 since the rolling element 50 gets off the projecting edge of the cam 51.

The disk B thus placed on the female mold 30 is then shaped into a pad by means of male mold 32.

Numeral 52 indicates a discharge device for taking the shaped pads P out of the shaping machine 25.

As shown in FIGS. 2 and 5, the discharge device 52 comprises a disk 54 driven by a drive mechanism 53 and formed with a cut 55 in the periphery thereof at equal angular intervals. When part of the periphery of the disk 54 comes to the position under the male mold 32 which is in its elevated position after shaping and the center of the male mold 32 still rotating comes in alignment with the cut 55, the suction is released and the pad P falls off the male mold and is received by the edge of the cut 55. The rotating disk 54 takes the pad P away from beneath the male mold 32. The pad P then abuts a fixed lever 56, falls on a belt conveyor 57, and is discharged.

Numeral 58 (FIG. 1) indicates an embossing machine, and 59 (FIG. 4) does a heating roller which intermittently moves up and down to temporarily seal the interior material to the waterproof paper 12.

What is claimed is:

1. An apparatus for manufacturing maternity pads, comprising a first die-cutting means for die-cutting a web of absorbent material of a predetermined thickness in the form of discs to obtain interior materials, a first transportation means for transporting said interior materials, a sealing means for sealing a waterproof paper to a covering material with said interior materials wrapped up between said waterproof paper and said covering material, a second die-cutting means for die-cutting the outer edge of the sealed portion of said waterproof paper and said covering material into a disk shape, a second transportation means for transporting said die-cut disks, a shaping means including pairs of vertically aligned male and female molds pivotably and radially arranged and actuators for pressing said male molds against said female molds for a predetermined period of time to form each disk interposed therebetween into a bowl shape with the side of said waterproof paper protruding, a feeder means for putting the disks on said second transportation means onto said female molds, and a discharge means for removing the shaped pads falling off said male molds after shaping the pads.

* * * * *